United States Patent
Samsonov et al.

(10) Patent No.: US 10,695,145 B2
(45) Date of Patent: Jun. 30, 2020

(54) TOMOGRAPHIC SCAN

(71) Applicant: CMT MEDICAL TECHNOLOGIES LTD., Yoqneam Ilit (IL)

(72) Inventors: Dmitry Samsonov, Maalot Tarshiha (IL); Ami Ben Hayun, Ramat Yishay (IL)

(73) Assignee: CMT MEDICAL TECHNOLOGIES LTD., Yoqneam Ilit (IL)

( * ) Notice: Subject to any disclaimer, the term of this patent is extended or adjusted under 35 U.S.C. 154(b) by 224 days.

(21) Appl. No.: 15/982,112

(22) Filed: May 17, 2018

(65) Prior Publication Data
US 2018/0263724 A1 Sep. 20, 2018

Related U.S. Application Data

(63) Continuation of application No. 15/017,644, filed on Feb. 7, 2016, now Pat. No. 10,143,532.
(Continued)

(51) Int. Cl.
| | |
|---|---|
| *A61B 17/58* | (2006.01) |
| *A61B 17/60* | (2006.01) |
| *A61B 90/00* | (2016.01) |
| *A61B 6/04* | (2006.01) |
| *A61B 6/02* | (2006.01) |
| *A61B 6/00* | (2006.01) |
| *G06T 11/00* | (2006.01) |

(52) U.S. Cl.
CPC .............. *A61B 90/39* (2016.02); *A61B 6/025* (2013.01); *A61B 6/0407* (2013.01); *A61B 6/44* (2013.01); *G06T 11/005* (2013.01); *A61B 2090/3937* (2016.02); *A61B 2090/3966* (2016.02); *G06T 2211/436* (2013.01)

(58) Field of Classification Search
CPC .......... A61B 2090/3966; A61B 6/0407; A61B 2090/3937; A61B 90/39; A61B 6/025; A61B 6/588; A61B 6/492; A61B 2034/206; G06T 3/00
See application file for complete search history.

(56) References Cited

U.S. PATENT DOCUMENTS

| | | |
|---|---|---|
| 5,285,785 A | 2/1994 | Meyer |
| 5,359,637 A | 10/1994 | Webber |

(Continued)

*Primary Examiner* — Don K Wong
(74) *Attorney, Agent, or Firm* — The Roy Gross Law Firm, LLC; Roy Gross

(57) ABSTRACT

A system for performing a scanning session of a patient's body, the system comprising: a radiation source; a radiation sensor; a patient positioner for placing the patient between the radiation source and the radiation sensor in a fixed position during each scan; at least one Pseudo-Random Grid (PRG) comprising randomly spaced perpendicular gridlines, the PRG being at least partially radiopaque and positioned between the radiation source and the radiation sensor in a fixed manner with respect to the patient positioner during the scanning session, wherein at least one of said radiation source and said radiation sensor is configured to move independently, and wherein at least one of said radiation source and said radiation sensor is moved to multiple different positions during the scanning session such that energy emitted from the radiation source passes through said PRG and said patient's body and collected by a surface of said radiation sensor.

6 Claims, 4 Drawing Sheets

Related U.S. Application Data

(60) Provisional application No. 62/114,906, filed on Feb. 11, 2015.

(56) References Cited

U.S. PATENT DOCUMENTS

| | | |
|---|---|---|
| 6,289,235 B1 | 9/2001 | Webber et al. |
| 6,888,924 B2 | 5/2005 | Claus et al. |
| 2011/0075238 A1* | 3/2011 | Sewell ................. G03F 9/7076 359/241 |
| 2011/0200169 A1 | 8/2011 | Oikawa |
| 2012/0014498 A1 | 1/2012 | Akahori |
| 2012/0087477 A1 | 4/2012 | Beck |
| 2013/0206985 A1 | 8/2013 | Turner et al. |
| 2014/0161352 A1 | 6/2014 | Buyens et al. |

* cited by examiner

TOMOGRAPHIC SCAN

RELATED APPLICATION

This application is a continuation of U.S. patent application Ser. No. 15/017,644 filed on Feb. 7, 2016, which claims the benefit of priority under 35 USC § 119(e) of U.S. Provisional Patent Application No. 62/114,906 filed on Feb. 11, 2015, the contents of which are incorporated herein by reference in their entirety.

FIELD OF THE INVENTION

The invention relates to the field of tomography.

BACKGROUND

Tomography may refer to imaging by sections or sectioning, through the use of any kind of penetrating wave Tomography may be used in radiology, archaeology, biology, atmospheric science, geophysics, oceanography, plasma physics, materials science, astrophysics, quantum information, and other sciences. In most cases it is based on the mathematical procedure called tomographic reconstruction.

Tomosynthesis is a method for performing high-resolution limited-angle tomography. Tomosynthesis dates back to the 1930s, where film-based radiography systems were used, with long exposure from a moving X-ray tube. Today, tomosynthesis combines digital image capturing and processing with simple tube/detector motion as used in conventional computerized tomography (CT). Although there are some similarities to CT, it is a separate technique. In CT, the source and detector make at least a 180-degree rotation about the subject, obtaining a complete set of data from which images may be reconstructed. In digital tomosynthesis, only a limited rotation angle (e.g., 15-60 degrees) may be used, with a relatively small number of discrete exposures (typically 10-80). This incomplete set of projections may be digitally processed to yield images, similar to conventional tomography but with a limited depth of field. However, because the image processing is digital, a series of slices at different depths and with different thicknesses may be reconstructed from the same acquisition, saving both time and radiation dose.

CT scans are typically performed by dedicated, high-end systems, with fast continuous rotations and with high-accuracy encoders for exact positioning of the system components. Tomosynthesis, on the other hand, is traditionally performed by simpler, less costly system, with compromised mechanical accuracy and robustness. Therefore, radiopaque objects ("fiducials") are commonly used in the tomosynthesis scans for better mutual alignment of the various views. Fiducial are generally fully opaque objects and therefore their trace may not be removed from the resulting image.

In the most general system, where both the detector and the X-ray source move freely, there are nine degrees-of-freedom (DOFs): three for the position of the detector center, three angular DOFs for the detector orientation in space and three for the X-ray source. Typically, a less general geometry is used, with up to eight DOFs, while one DOF is being held fixed. For example, the distance between the source and the detector might be kept constant. For that purpose, at least four fiducial points have to be used, each contributing two independent measures of x- and y-coordinates. However, more fiducials are typically used.

U.S. Pat. No. 5,359,637 to Webber discloses a self-calibrating tomosynthetic x-ray system. A calibrated device for recording radiographic images of a selected object irradiated by a source of radiation includes a first radiolucent radiographic recording medium in the form of a CCD device for recording a first projected radiographic image of the selected object. A second radiographic recording medium in the form of a CCD device is supported in fixed generally parallel position relative to the first radiographic recording medium to permit radiation from the source to pass through the first radiographic recording medium and to impinge upon the second radiographic recording medium for recording a second projected radiographic image of the selected object. A radiopaque fiducial reference in the form of a grid is supported in fixed position generally between the first and second radiographic recording mediums to permit a projected image of the radiopaque fiducial reference to be recorded on the second radiographic recording medium. Projected radiographic images of the object and the fiducial reference are then recorded at different arbitrary relative positions between the source of radiation and the object, the fiducial reference, and the recording mediums. An image of a selected object at a selected slice position through the object is synthesized from selected projected radiographic images of the object and the fiducial reference recorded by the calibrated device.

U.S. Pat. No. 6,888,924 to Claus et al. discloses geometry of a tomosynthesis system including a detector and an x-ray source, which is determined using fiducial markers with non-determined positions. The geometry is determined by arbitrarily identifying at least two markers within an imaged volume, at different relative distances between the detector and the x-ray source, without having projections located on a straight line for all different source positions, and locating the projections of the markers within at least two images acquired of the imaged volume. The at least two images correspond to different positions of a focal spot of the x-ray source.

US Patent Application Publication No. 2012/0014498 to Akahori discloses a radiographic imaging apparatus which includes: a radiation source for applying radiation to a subject and at least one marker; a detecting unit for detecting the radiation transmitted through the subject; and an image obtaining unit for moving the radiation source relative to the detecting means, applying the radiation to the subject from a plurality of radiation source positions provided by the movement of the radiation source, and obtaining a plurality of images corresponding respectively to the radiation source positions. The apparatus further includes a radiation source position obtaining unit for obtaining positional information of each radiation source position of interest relative to a reference radiation source position among the radiation source positions based on at least one marker image contained in each of a reference image obtained with the reference radiation source position and an image of interest obtained with the radiation source position of interest.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a system for performing a scanning session of at least a portion of the body of a patient, the system comprising: a radiation source; a radiation sensor; a patient positioner for placing the patient between the radiation source and the radiation sensor in a fixed position during each scan of the scanning session; at least one pseudo-random grid comprising randomly spaced perpendicular gridlines, the pseudo-random grid being at least partially radiopaque and positioned between the radiation source and the radiation sensor in a fixed manner with respect to the patient positioner during the scanning session, wherein at least one of said radiation source and said radiation sensor is configured to move independently, and wherein at least one of said radiation source and said radiation sensor is moved to multiple different positions during the scanning session such that energy emitted from the radiation source passes at least partially through said pseudo-random grid and said at least a portion of the body of the patient and collected by a surface of said radiation sensor.

There is provided, in accordance with another embodiment, an add-on to an imaging system comprising: at least one pseudo-random grid comprising perpendicular gridlines which are randomly spaced, the pseudo-random grid being at least partially radiopaque; and a mount for coupling the pseudo-random grid with the imaging system.

There is provided, in accordance with a further embodiment, a method for performing a scan session of at least a portion of the body of a patient, the method comprising: positioning at least one pseudo-random grid, at least partially radioopaque, in a fixed position with respect to a position of the patient, wherein the pseudo-random grid comprises perpendicular gridlines which are randomly spaced, multiply positioning at least one of a radiation source and a radiation sensor during the scanning session, wherein a corresponding at least one of the radiation source and the radiation sensor is configured to move independently, to obtain multiple scans of said at least portion of the body of said patient, wherein said at least one pseudo-random grid is at least partially imaged in said multiple scans; and obtaining said multiple scans of said at least portion of the body of said patient.

There is provided, in accordance with yet another embodiment, a method for evaluating the geometry of a projection of a fiducial marker in an image, wherein the fiducial marker is an alignment grid comprising perpendicular gridlines, the alignment grid being at least partially radiopaque, the method comprising using at least one hardware processor for: identifying straight lines in the image; identifying a first set of parallel lines of said straight lines by iteratively determining which of said straight lines converge to the same point, wherein said first set of parallel lines represents a first group of parallel gridlines of said perpendicular gridlines; identifying a second set of parallel lines from the remainder of said straight lines by iteratively determining which of said remainder of said straight lines approximately converge to the same point, wherein said second set of parallel lines represents a second group of parallel gridlines of said perpendicular gridlines which are perpendicular to the first group of parallel gridlines; calculating feature points by calculating intersection points between the first set of parallel lines and the second set of parallel lines; and evaluating a homographic matrix for transforming the space of the image to a reference frame of the fiducial marker by correlating the feature points to the intersection points of the perpendicular gridlines of the fiducial marker.

There is provided, in accordance with yet a further embodiment, a computer program product for evaluating the geometry of a projection of a fiducial marker in an image, wherein the fiducial marker is an alignment grid comprising perpendicular gridlines, the alignment grid being at least partially radiopaque, the computer program product comprising a non-transitory computer-readable storage medium having program code embodied therewith, the program code executable by at least one hardware processor to: identify straight lines in the image; identify a first set of parallel lines of said straight lines by iteratively determining which of said straight lines approximately converge to the same point, wherein said first set of parallel lines represents a first group of parallel gridlines of said perpendicular gridlines; identify a second set of parallel lines from the remainder of said straight lines by iteratively determining which of said remainder of said straight lines approximately converge to the same point, wherein said second set of parallel lines represents a second group of parallel gridlines of said perpendicular gridlines which are perpendicular to the first group of parallel gridlines; calculate feature points by calculating intersection points between the first set of parallel lines and the second set of parallel lines; and evaluate a homographic matrix for transforming the space of the image to a reference frame of the fiducial marker by correlating the feature points to the intersection points of the perpendicular gridlines of the fiducial marker.

In some embodiments, the pseudo-random grid is tilted with respect to the surface of said radiation sensor.

In some embodiments, the system has nine degrees of freedom comprising three translational degrees of freedom of said radiation sensor, three rotational degrees of freedom of said radiation sensor and three translational degrees of freedom of said radiation source.

In some embodiments, one or more of said nine degrees of freedom is held fixed.

In some embodiments, the one or more degrees of freedom which are held fixed relate to constraints selected from the group consisting of: a constant distance between the radiation source and the center of the radiation sensor, a tilt angle of the radiation sensor, confining the motion of the radiation sensor to a predefined plane, setting the projection of the radiation source to coincide with the center of the radiation sensor and a motion of the radiation sensor being dependent on the motion of the radiation source.

In some embodiments, the one or more degrees of freedom which are held fixed relate to a motion of the radiation sensor being dependent on the motion of the radiation source, a guide point in space is selected, and the motion of the radiation sensor is set to keep a constant magnification of said guide point.

In some embodiments, the one or more degrees of freedom which are held fixed relate to a motion of the radiation sensor being dependent on the motion of the radiation source, a guide point in space is selected, and the radiation sensor is placed such that radiation emanating from said radiation source and crossing the guide point hits a constant pixel of the radiation sensor.

In some embodiments, the at least one pseudo-random grid comprises two or more pseudo-random grids, and wherein at least two of said two or more pseudo-random grids are tilted one with respect to the other in one or more predefined angles correspondingly.

In some embodiments, the method further comprises using at least one hardware processor for: evaluating the geometry of a projection of said at least one Pseudo-random grid in each one of said multiple scans for registering said multiple scans; and performing image reconstruction based on said registering of said multiple scans.

In some embodiments, the evaluating of the geometry of the projection of said at least one pseudo-random grid in each one of said multiple scans comprises further using said at least one hardware processor with respect to each scan of said multiple scans for: identifying straight lines in the scan; identifying a first set of parallel lines of said straight lines by iteratively determining which of said straight lines approximately converge to the same point, wherein said first set of parallel lines represents a first group of parallel gridlines of said perpendicular gridlines; identifying a second set of parallel lines from the remainder of said straight lines by iteratively determining which of said remainder of said straight lines approximately converge to the same point, wherein said second set of parallel lines represents a second group of parallel gridlines of said perpendicular gridlines which are perpendicular to the first group of parallel gridlines; calculating feature points by calculating intersection points between the first set of parallel lines and the second set of parallel lines; and evaluating a homographic matrix for transforming the space of the scan to a reference frame of the at least one pseudo-random grid by correlating the feature points to the intersection points of gridlines of the at least one pseudo-random grid.

In some embodiments, the identification of a first set of parallel lines of said straight lines is performed by: performing for each two straight lines of the identified straight lines the following steps: a. computing the convergence point of the two straight lines, b. determining each one of the straight lines, as an inlier, if it approximately converges to said convergence point, or as an outlier, if it does not, to receive a current division of the straight lines into inliers and outliers, c. calculating the average convergence point of the inliers and determining it to be the current convergence point, and d. iteratively dividing the inliers into current inliers and outliers based on the current convergence point and iteratively computing the current convergence point based on the current inliers to receive a final division of the straight lines into inliers and outliers associated with said two straight lines and with said current convergence point, and identifying the current convergence point associated with the final division having the least number of outliers, wherein the inliers of said final division having the least number of outliers are identified as the first set of parallel lines of said straight lines, and wherein the identification of said second set of parallel lines from the remainder of said straight lines is performed by: performing said steps a to d for each two straight lines of the remainder of said straight lines, and identifying the current convergence point which is associated with the final division having the least number of outliers, wherein the inliers of said final division having the least number of outliers are identified as the second set of parallel lines.

In some embodiments, the at least one pseudo-random grid comprises perpendicular gridlines which are randomly spaced.

In some embodiments, the identifying of the lines in the image is performed by applying the Hough transform to the image.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

The disclosed tomographic scan may produce three-dimensional (3D) images of body portions of a patient. The disclosed tomographic scan may utilize one or more fiducial markers in the form of a grid (i.e., a network of perpendicular lines), which are termed herein below as "alignment grids". These alignment grids may also be pseudo-random grids by irregularly spacing their gridlines to receive a marker which may be uniquely identified even if only partially scanned.

The disclosed alignment grids may be an integral part of disclosed imaging systems or add-ons to existing imaging systems. A radiation source and a radiation sensor (e.g. FPD) of the disclosed imaging systems or of existing imaging systems, such as tomosynthesis imaging systems, may be moved and rotated in relation to one another in an independent manner and with up to nine degrees of freedom while taking multiple images. The images (with the one or more alignment grids shadows in them) may be then synthesized into 3D, resulting, for example, in a semi-CT result, when X-ray imaging is concerned. An algorithm for retrieving the trace of the disclosed alignment grid relative to a reference frame in order to perform image registration is also disclosed.

For example, tomosynthesis procedures are of low-dose in nature (typically, dose of tomosynthesis view is about 1% of the standard radiography dose), thus the noise level may be very high (e.g., ten times higher). Since in the disclosed alignment grid all the radiopaque points are located along straight lines, the task of differentiating between the grid points and the noise may be much easier. Hence, there is no need to use the known strategies of using a large number of small fiducial markers or large fiducial markers in order to overcome the noise. These strategies may harden the task of differentiating and locating of the markers in the image. Thus, using the disclosed alignment grids may improve the positioning accuracy, because opaque lines may be made very thin and still may be accurately evaluated. As opposed to that, using many small fiducials may be disrupted by noise-originated outliers and using large fiducials may not provide the required geometrical resolution. Using a large number of fiducial markers in a noise-contaminated system may affect feasibility and reliability of the retrieving algorithm.

The term "scanning session", as referred to herein, may relate to a session in which at least one scan is performed.

The terms "image" and "scan" and their derivations may be used herein below in an interchangeable manner.

Figure 1:
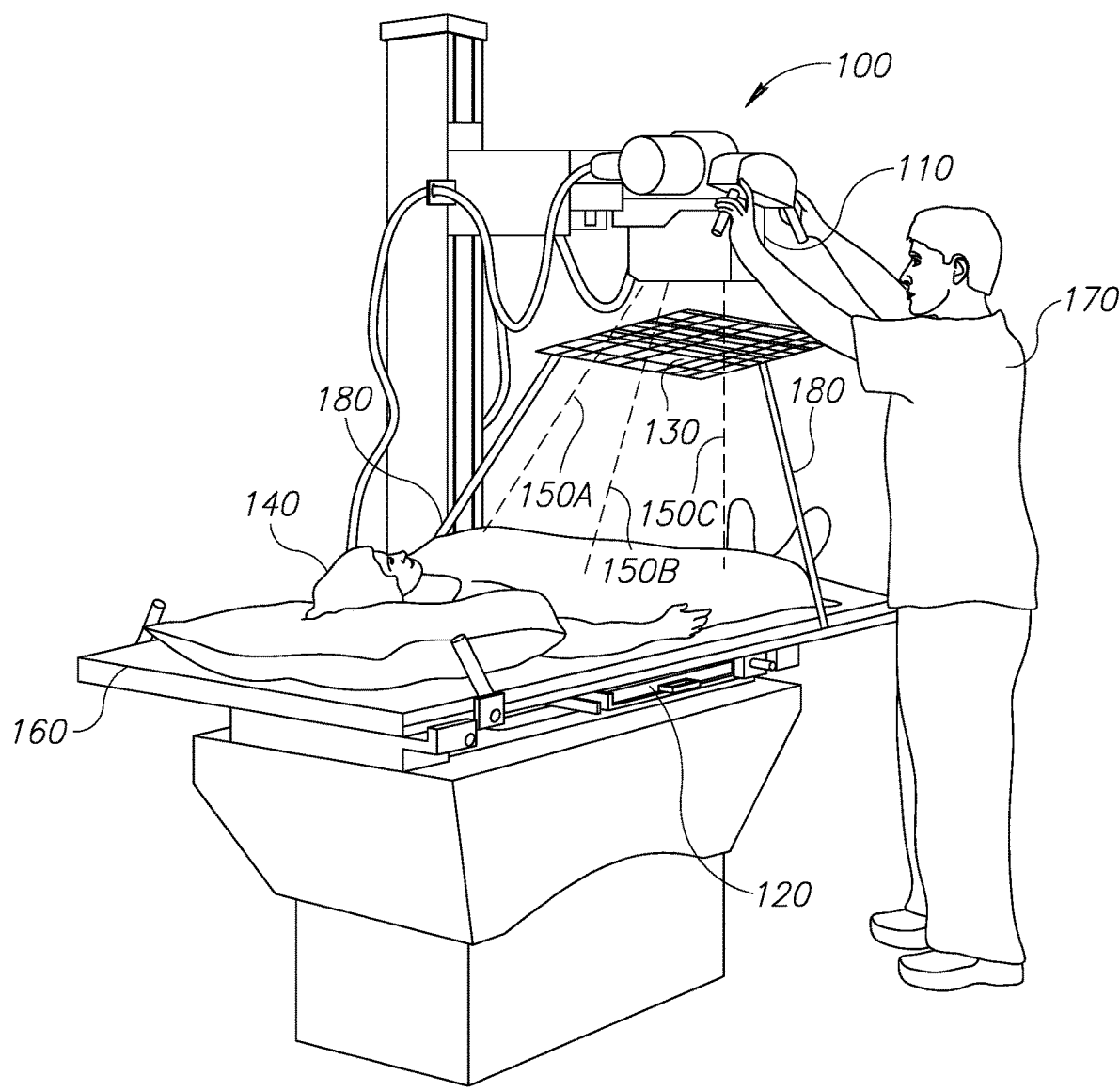
FIG. 1 shows an exemplary add-on to an imaging system for performing a tomosynthesis scanning session of at least a portion of the body of a patient according to an embodiment.

Reference is now made to FIG. 1, which shows an exemplary add-on to an imaging system 100 for performing a tomosynthesis scanning session of at least a portion of the body of a patient according to an embodiment.

In general, system 100 may be in accordance with medical imaging systems as known in the art, such as X-ray or CT systems. In particular, system 100 may be in accordance with prior art imaging systems, specifically old prior art imaging systems such as an X-ray device, C-arm or U-arm or a full-rotation CT device.

System 100 may include a radiation source 110 and a radiation sensor 120. System 100 may further include a patient positioner, such as bed 160. Radiation source 110, radiation sensor 120, and bed 160 may or may not be coupled with each other. System 100 may be operated by an operator 170, which may be, for example, a technician or a care giver. An alignment grid 130 may be an integral part of system 100 or may be coupled with system 100 as an add-on, as shown in FIG. 1. The following description will refer to alignment grid 130 as an add-on to system 100, where system 100 is an existing imaging system. However, the following description also refers to an imaging system which includes the alignment grid as an integral part with the required modifications.

The add-on may further include a mount for coupling the imaging system with the alignment grid. Thus, system 100 may be coupled with alignment grid 130 via a mount 180. Mount 180 may mount alignment grid 130 to the patient positioner, i.e., bed 160. Mount 180 may include two rigid or flexible stripes which may clip to alignment grid 130 at one end and to the patient positioned at the other end. Mount 180 may be of other forms, as known in the art, such as an arm. Alignment grid 130 may be disposed between radiation source 110 and radiation sensor 120. Patient 140 may be positioned between radiation source 110 and radiation sensor 120. Alignment grid 130 may be located by mount 180 in a fixed position with respect to patient 140 and the patient positioner. This is in order to allow registration of the different image views of patient 140 received in the scan session based on alignment grid 130. Alignment grid 130 may be located such that radiation emitted from radiation source 110 towards the desired body portion of patient 140, at least partially pass through it. For example, alignment grid 130 may be located between patient 140 and radiation source 110, as shown in FIG. 1. Alternatively, alignment grid 130 may be located between patient 140 and radiation sensor 120. For example, as shown in FIG. 1, radiation source 110 may be positioned above patient 140, radiation sensor 120 may be positioned below patient 140 and alignment grid 130 may be positioned between radiation source 110 and patient 140.

Radiation source 110 and/or radiation sensor 120 may be configured to move independently during the scanning session. Accordingly, radiation source 110 and/or radiation sensor 120 may be moved to multiple different positions, by that forming various dispositions of system 100, during the scanning session. Thus, a set of images may be formed, including traces of the patient and the alignment grid, as projected through plurality of viewing angles and imaging magnifications.

System 100 may have nine degrees of freedom which include three translational degrees of freedom and three rotational degrees of freedom of radiation sensor 120, and three translational degrees of freedom of radiation source 110. In some embodiments, one or more of the nine degrees of freedom may be held fixed. This limitation may be achieved, for example, by keeping one degree of freedom degenerate or by restricting the mutual radiation source-radiation sensor motions. A degree of freedom which may be held fixed may relate to constraints such as: a constant distance between radiation source 110 and the center of radiation sensor 120, a tilt angle of radiation sensor 120 (i.e., allowing only two rotational degrees of freedom), confining the motion of radiation sensor 120 to a predefined plane (i.e., allowing only two translational degrees of freedom), setting the projection of radiation source 110 to coincide with the center of radiation sensor 120 and a motion of radiation sensor 120 being dependent on the motion of radiation source 110.

If the degree of freedom which is held fixed relates to the constraint of a motion of radiation sensor 120 being dependent on the motion of radiation source 110, a guide point in space may be selected. In some embodiments, the motion of radiation sensor 120 may be set to keep a constant magnification of the guide point. In some other embodiments, radiation sensor 120 may be placed such that radiation emanating from radiation source 110 and crossing the guide point hits a constant pixel of radiation sensor 120.

At least one of radiation source 110 and radiation sensor 120 may be moved to multiple different positions during the scanning session in which energy emitted from radiation source 110, such as energy beams 150A, 150B and 150C, pass at least partially through alignment grid 130 and the desired body portion of patient 140 and collected by a surface of radiation sensor 120. As detailed herein above, alignment grid 130 remains in a fixed position with respect to the position of patient 140 during the entire scanning session.

Radiation source 110 may be, for example, an X-ray radiation source. Radiation sensor 120 may be a flat panel detector (FPD).

Alignment grid 130 may be typically a rectangular sheet of transparent material, such as glass, plastic or Carbon sheet, having formed thereon a grid (i.e., perpendicular gridlines), e.g., by printing or other form of material deposition. The gridlines of alignment grid 130 may be at least partially radiopaque. The gridlines of alignment grid 130 may be made of less-absorbing material, comparing to common fiducial markers, because fewer points may be required for the definition of a straight line. Accordingly, the gridlines may block between 5% and 30% of the radiation beam. In some embodiments, the gridlines may block between 5% and 10% of the radiation beam. In some embodiments, the gridlines may block between 10% and 20% of the radiation beam. In some embodiments, the gridlines may block between 20% and 30% of the radiation beam. In some embodiments, the gridlines may block at least 5% of the radiation, at least 10% of the radiation, at least 20% of the radiation or at least 30% of the radiation. Thus, the gridlines may not fully block the radiation impinging them. In addition, due to the partial radiopaqueness, one may still see what lies beneath the gridlines and the gridlines may be more easily removed from the image to produce a clear image of a body portion of a patient.

Alignment grid 130 may be positioned such that its plane is parallel or tilted with respect to the surface of radiation sensor 120. Alignment grid 130 may be disposed between radiation source 110 and radiation sensor 120, such that the resulting scan shows the shadow of alignment grid 130. Since the relative location of patient 140 and alignment grid 130 is fixed during the scanning session, one may use alignment grid 130 to perform image registration to the scans received in each scanning session.

Figure 2:
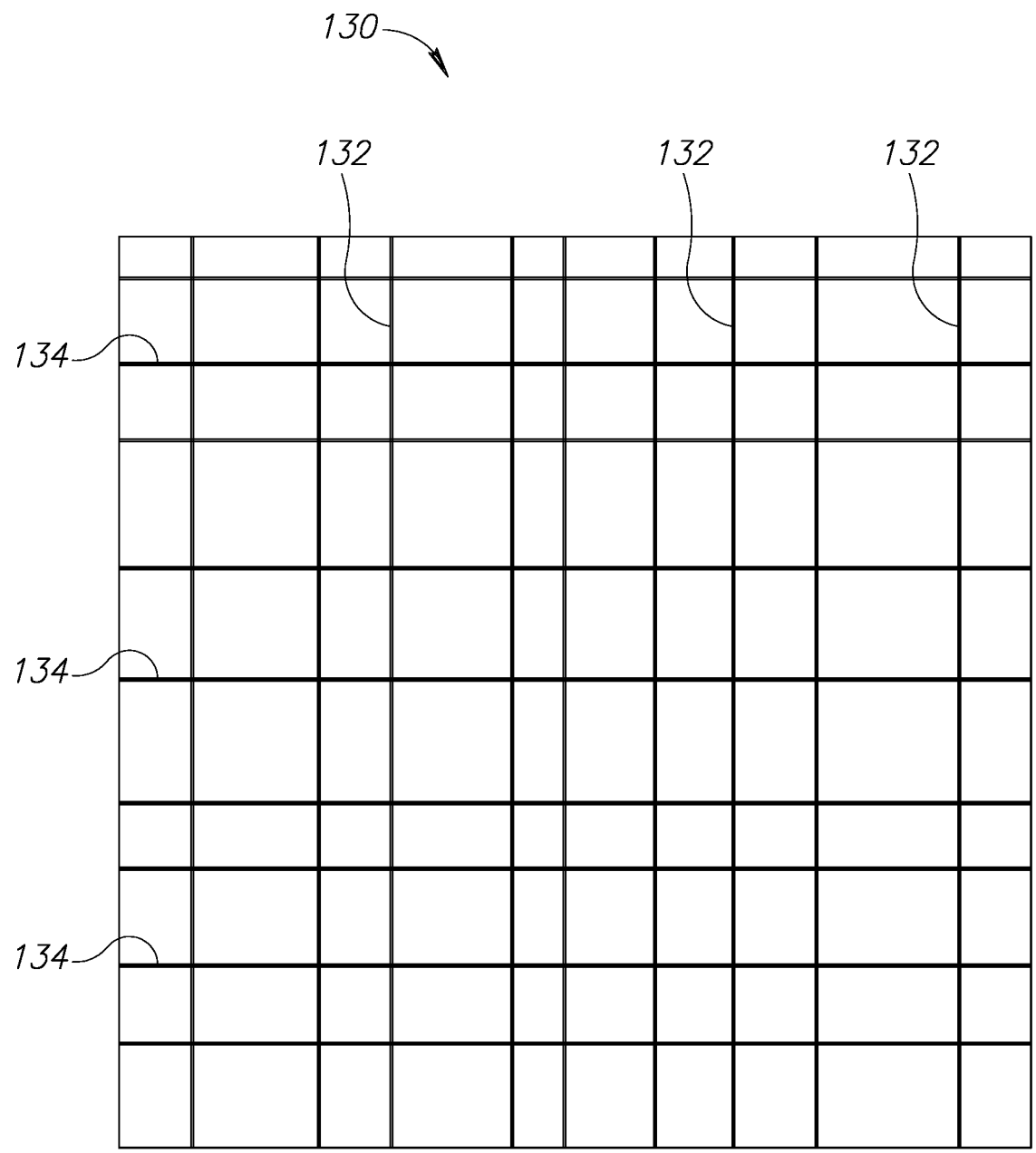
FIG. 2 shows a pseudo-random grid of the exemplary add-on of FIG. 1.

In some embodiments, alignment grid 130 may be a Pseudo-Random Grid (PRG) which includes gridlines which are randomly spaced. In some embodiments, the set of distances between neighboring pairs of the randomly spaced gridlines may be a random set of different numbers. Therefore, when the RPG is projected upon radiation sensor 120, two sets of mutually-perpendicular converging lines are formed, each of which is pseudo-randomly spaced. Since the gridlines are randomly-spaced, the PRG position may be evaluated even if it is only partially imaged. Reference is now made to FIG. 2, which shows pseudo-random grid 130 of the exemplary add-on of FIG. 1. PRG 130 may include gridlines indicated 132 and 134. Gridlines 132 may form a first set of parallel straight lines and gridlines 134 may form a second set of parallel straight lines, while gridlines 132 are perpendicular to gridlines 134 and vice versa. Gridlines 132 and 134 may be randomly spaced, i.e., the spaces between gridlines 132 and the spaces between gridlines 134 are not constant. In some embodiments, only gridlines 132 or gridlines 134 may be randomly spaced. In some embodiments only a portion of gridlines 132 and/or 134 may be randomly spaced. It should be noted that by referring herein to a grid as "randomly spaced" it is meant that at least a portion of one set of the two sets of parallel gridlines is randomly spaced.

In some embodiments, system 100 may include two or more alignment grids such as alignment grid 130, located in different positions with respect to one or more body portions of interest of patient 140. At least two of the two or more alignment grids may be tilted one with respect to the other in one or more predefined angles, correspondingly. Such configuration may be advantageous, for example, when using an imaging system with nine DOFs.

The patient positioner may be configured to hold the patient in a fixed manner during the scanning session. The patient positioner may be, for example, bed 160, a chair or any other fixture for this purpose.

Using alignment grid 130 may enhance the imaging accuracy and may save the need for relatively expensive encoders.

Figure 3:
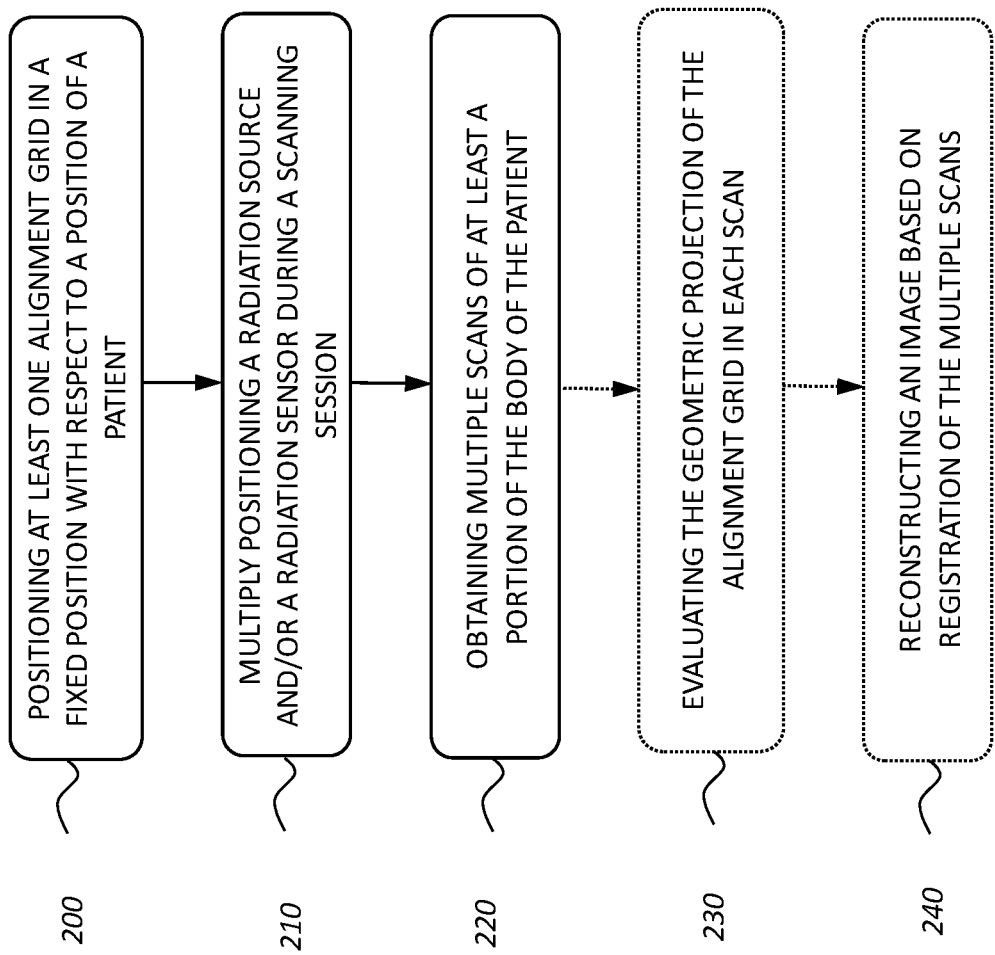
FIG. 3 shows a flowchart of a method for performing a scan session of at least a portion of the body of a patient, constructed and operative in accordance with an embodiment of the disclosed technique.

Reference is now made to FIG. 3, which shows a flow-chart of a method for performing a scan session of at least a portion of the body of a patient, constructed and operative in accordance with an embodiment of the disclosed technique.

In a step 200, at least one alignment grid, at least partially radiopaque, may be positioned in a fixed position with respect to a position of the patient. The alignment grid may include a network of perpendicular gridlines. The alignment grid may be similar to alignment grid 130 of system 100 of FIGS. 1 and 2. With reference to FIG. 1, alignment grid 130 may be positioned in a fixed manner above a portion of the body of patient 140 to be scanned.

In a step 210, a radiation source and/or a radiation sensor may be multiply positioned during the scanning session. The radiation source and/or the radiation sensor may be configured to move independently, to obtain multiple scans of the at least portion of the body of the patient. The at least one alignment grid may be at least partially imaged in the multiple scans. The radiation source and the radiation sensor may be similar to and may be moved in accordance with radiation source 110 and radiation sensor 120 of system 100 of FIG. 1. With reference to FIG. 1, radiation source 110 is positioned above a portion of the patient's body of interest. Radiation sensor 120 may be positioned beneath the portion of the patient's body of interest.

In a step 220, multiple scans of the at least portion of the body of the patient may be obtained. Such multiple scans may be obtained, for example, by using system 100 of FIG. 1 and according to techniques known in the art.

In an optional step 230, the geometry of a projection of the at least one alignment grid in each one of the multiple scans may be evaluated for the purpose of registering the multiple scans. A method for evaluating the geometry of the projection of an alignment grid in a scan is disclosed below with respect to FIG. 4.

In an optional step 240, image reconstruction may be performed based on the registration of the multiple scans. The image reconstruction may be performed according to any of the prior art techniques such as shift-and-add, filtered back-projection or algebraic method.

Figure 4:
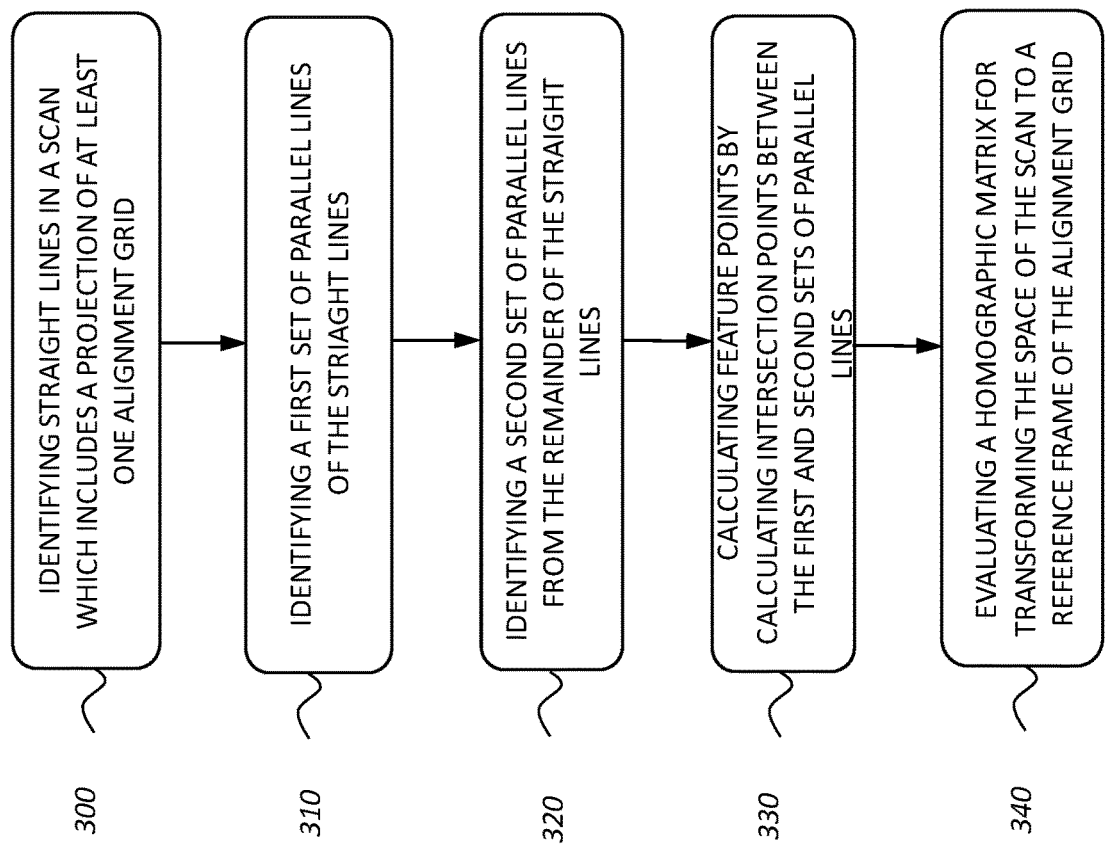
FIG. 4 shows a flowchart of a method for evaluating of the geometry of the projection of an alignment grid in a scan, constructed and operative in accordance with an embodiment of the disclosed technique.

Reference is now made to FIG. 4, which shows a flow-chart of a method for evaluating the geometry of the projection of an alignment grid in a scan, constructed and operative in accordance with an embodiment of the disclosed technique.

The method of FIG. 4 may be used to perform step 240 of the method of FIG. 3 by performing the method of FIG. 4 with respect to each scan of the multiple scans. Alternatively, the method of FIG. 4 may be used independently for evaluating the geometry of a projection of a fiducial marker in an image, where the fiducial marker is in the form of a grid and includes a network of perpendicular gridlines.

In a step 300, straight lines in the scan may be identified. The identifying of the lines in the scan may be performed by applying Hough transform to the scan. One may then consider the transform-points which are stronger than a certain predefined threshold.

However, few or more lines might be seen that are not related to the alignment grid. Further, the scan may be noisy, so few or more of the true gridlines of the alignment grid may be masked by noise. Therefore, the following steps are aimed at iteratively estimating the lines.

In a step 310, a first set of straight lines may be identified by iteratively determining which of the straight lines converge to the same point. The first set of lines may represent a first group of parallel gridlines of the perpendicular gridlines of the alignment grid.

The identification of the first set of parallel lines may be performed by performing the following steps for each two straight lines of the identified straight lines.

In a first step, the convergence point of the two straight lines may be computed.

In a second step, each one of the straight lines may be determined as an inlier, if it approximately (i.e., up to a predefined threshold) converges to the convergence point, or as an outlier, if it does not. Thus, a current division of the straight lines into inliers and outliers may be received.

In a third step, the average convergence point of all the inliers (i.e., an average of the convergence points of all the inliers) may be calculated and determined to be the current convergence point.

In a forth step, the inliers may be iteratively divided into current inliers and outliers based on the current convergence point. The current convergence point may be iteratively computed based on the current inliers. This iterative process may continue until convergence into the actual inliers is achieved. Thus, a final division of the straight lines into inliers and outliers, associated with the two straight lines and the current convergence point, may be received.

Then, the current convergence point which is associated with the final division that has the least number of outliers may be identified. The inliers of such final division may be identified as the first set of parallel lines.

In a step 320, a second set of parallel lines from the remainder of the straight lines may be identified by iteratively determining which of the remainder of the straight lines approximately converge to the same point (i.e., up to a predefined threshold). By "the remainder of the straight lines" it is meant the straight lines which are left after removing the first set of parallel lines from the identified straight lines. The second set of parallel lines may represent a second group of parallel gridlines which are perpendicular to the first group of parallel gridlines. The identification of the second set of parallel lines from the remainder of the straight lines may be performed by repeating the above steps detailed with respect to the identification of the first set of parallel lines. These steps may be performed for each two straight lines of the remainder of the straight lines. The current convergence point which is associated with the final division that has the least number of outliers may be identified. The inliers of such a final division may be identified as the second set of parallel lines.

In a step 330, feature points may be calculated by calculating intersection points between the first set of parallel lines and the second set of parallel lines. This may be performed by running over all pairs of lines in a grid formed by the identified perpendicular first and second sets of parallel lines and calculating all the cross-section points (i.e., the feature points). These intersection points may be used as fiducials for image registration.

In a step 340, a homographic matrix (of 3*3 dimensions) for transforming the space of the scan to a reference frame of the at least one alignment grid may be evaluated by correlating the feature points to the intersection points of gridlines of the at least one alignment grid. If the alignment grid is a PRG, then the feature points may be uniquely correlated to their respective intersection gridline points.

System 100 of FIG. 1 may operate according to the method of FIG. 3. System 100 of FIG. 1 may further include at least one hardware processor configured to execute dedicated software in order to perform optional steps 240 and 250 of the method of FIG. 3 and/or perform the method of FIG. 4. System 100 may then include a storage device for storing the dedicated software.

It is preferable to remove the traces of the alignment grid (or of a fiducial marker) from the scans before reconstructing the 3D image. Such task may be easier since the alignment grid, being comprised of straight lines, may be made of less-absorbing material. Hence, its projection (i.e., shadow) in the scans tends to be more faint. In addition, typically, one may utilize information of neighboring (uncovered) pixels for such task. A fiducial pixel might be surrounded by many other fiducial pixels. On the other hand, a pixel of a gridline may typically have six neighboring pixels that may be uncovered by the gridline.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for evaluating the geometry of a projection of a fiducial marker in an image, wherein the fiducial marker is an alignment grid comprising perpendicular gridlines, the alignment grid being at least partially radiopaque, the method comprising using at least one hardware processor for:

identifying straight lines in the image;

identifying a first set of parallel lines of said straight lines by iteratively determining which of said straight lines converge to the same point, wherein said first set of parallel lines represents a first group of parallel gridlines of said perpendicular gridlines;

identifying a second set of parallel lines from the remainder of said straight lines by iteratively determining which of said remainder of said straight lines approximately converge to the same point, wherein said second set of parallel lines represents a second group of parallel gridlines of said perpendicular gridlines which are perpendicular to the first group of parallel gridlines;

calculating feature points by calculating intersection points between the first set of parallel lines and the second set of parallel lines; and evaluating a homographic matrix for transforming the space of the image to a reference frame of the fiducial marker by correlating the feature points to the intersection points of the perpendicular gridlines of the fiducial marker.

2. The method of claim 1, wherein the identifying of the lines in the image is performed by applying the Hough transform to the image.

3. The method of claim 1, wherein the identification of a first set of parallel lines of said straight lines is performed by:

performing for each two straight lines of the identified straight lines the following steps:

a. computing the convergence point of the two straight lines, b. determining each one of the straight lines, as an inlier, if it approximately converges to said convergence point, or as an outlier, if it does not, to receive a current division of the straight lines into inliers and outliers, c. calculating the average convergence point of the inliers and determining it to be the current convergence point, and d. iteratively dividing the inliers into current inliers and outliers based on the current convergence point and iteratively computing the current convergence point based on the current inliers to receive a final division of the straight lines into inliers and outliers associated with said two straight lines and with said current convergence point, and identifying the current convergence point associated with the final division having the least number of outliers, wherein the inliers of said final division having the least number of outliers are identified as the first set of parallel lines of said straight lines, and wherein the identification of said second set of parallel lines from the remainder of said straight lines is performed by:

performing said steps a to d for each two straight lines of the remainder of said straight lines, and identifying the current convergence point which is associated with the final division having the least number of outliers, wherein the inliers of said final division having the least number of outliers are identified as the second set of parallel lines.

4. A computer program product for evaluating the geometry of a projection of a fiducial marker in an image, wherein the fiducial marker is an alignment grid comprising perpendicular gridlines, the alignment grid being at least partially radiopaque, the computer program product comprising a non-transitory computer-readable storage medium having program code embodied therewith, the program code executable by at least one hardware processor to:
    identify straight lines in the image;
        identify a first set of parallel lines of said straight lines by iteratively determining which of said straight lines approximately converge to the same point, wherein said first set of parallel lines represents a first group of parallel gridlines of said perpendicular gridlines;
        identify a second set of parallel lines from the remainder of said straight lines by iteratively determining which of said remainder of said straight lines approximately converge to the same point, wherein said second set of parallel lines represents a second group of parallel gridlines of said perpendicular gridlines which are perpendicular to the first group of parallel gridlines;
    calculate feature points by calculating intersection points between the first set of parallel lines and the second set of parallel lines; and
    evaluate a homographic matrix for transforming the space of the image to a reference frame of the fiducial marker by correlating the feature points to the intersection points of the perpendicular gridlines of the fiducial marker.

5. The computer program product of claim 4, wherein the identification of the lines in the image is performed by applying the Hough transform to the image.

6. The computer program product of claim 4, wherein the identification of a first set of parallel lines of said straight lines is performed by:
    performing for each two straight lines of the identified straight lines the following steps:
        a. computing the convergence point of the two straight lines,
        b. determining each one of the straight lines, as an inlier, if it approximately converges to said convergence point, or as an outlier, if it does not, to receive a current division of the straight lines into inliers and outliers,
        c. calculating the average convergence point of the inliers to be the current convergence point, and
        d. iteratively dividing the inliers into current inliers and outliers based on the current convergence point and iteratively computing the current convergence point based on the current inliers to receive a final division of the straight lines into inliers and outliers associated with said two straight lines and with said current convergence point, and
    identifying the current convergence point which is associated with the final division having the least number of outliers, wherein the inliers of said final division having the least number of outliers are identified as the first set of parallel lines of said straight lines,
and wherein the identification of said second set of parallel lines from the remainder of said straight lines is performed by:
performing said steps a to d for each two straight lines of the remainder of said straight lines, and
identifying the current convergence point which is associated with the final division having the least number of outliers, wherein the inliers of said final division having the least number of outliers are identified as the second set of parallel lines.

\* \* \* \* \*